(12) United States Patent
Botzem et al.

(10) Patent No.: US 6,527,932 B1
(45) Date of Patent: Mar. 4, 2003

(54) METHODS FOR PRODUCING OR PURIFYING ONIUM HYDROXIDES BY MEANS OF ELECTRODIALYSIS

(75) Inventors: Jörg Botzem, Limburgerhof (DE); Reiner Kober, Fussgönheim (DE); Markus Frede, Eppelheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/856,461

(22) PCT Filed: Dec. 6, 1999

(86) PCT No.: PCT/EP99/09515

§ 371 (c)(1),
(2), (4) Date: Jun. 7, 2001

(87) PCT Pub. No.: WO00/34224

PCT Pub. Date: Jun. 15, 2000

(30) Foreign Application Priority Data

Dec. 7, 1998 (DE) .......................... 198 56 376

(51) Int. Cl.[7] .............................. B01D 61/44
(52) U.S. Cl. .............. 204/534; 204/537; 204/541
(58) Field of Search ................. 204/534, 537, 204/541

(56) References Cited

U.S. PATENT DOCUMENTS

| 4,578,161 A | 3/1986 | Buonomo et al. |
| 5,286,354 A | 2/1994 | Bard et al. |
| 5,389,211 A | 2/1995 | Sharifian et al. |

FOREIGN PATENT DOCUMENTS

| EP | 0 834 345 | 4/1998 |
| EP | 0 834 346 | 4/1998 |
| EP | 0 870 532 | 10/1998 |
| WO | WO 88/07975 | 10/1988 |
| WO | WO 98/09002 | 3/1998 |
| WO | WO 98/44169 | 10/1998 |

OTHER PUBLICATIONS

J. R. Ochoa Gomez, et al., Journal of Applied Electrochemistry, vol. 21, pp. 365–367, "Electrosynthesis of Quaternary Ammonium Hydroxides", 1991.

*Primary Examiner*—Arun S. Phasge
(74) *Attorney, Agent, or Firm*—Oblon, Spivak, McClelland, Maier & Neustadt, P.C.

(57) ABSTRACT

Methods of preparing or purifying onium hydroxides of the elements N, S or P by electrodialysis involve an electrodialysis apparatus comprising one or more cell units, each cell unit comprising a bipolar membrane and an anion-selective membrane, and a bipolar membrane or a cation-selective membrane being located on the anode side between the last anion-selective membrane and the anode.

25 Claims, 1 Drawing Sheet

METHODS FOR PRODUCING OR PURIFYING ONIUM HYDROXIDES BY MEANS OF ELECTRODIALYSIS

The present invention relates to methods of preparing or purifying onium hydroxides of the elements N, S or P by electrodialysis in an electrodialysis apparatus comprising one or more cell units, each cell unit comprising a bipolar membrane and an anion-selective membrane.

Stable or at least largely stable onium compounds, i.e. the onium compounds of the elements N, S and P, play a major part in many fields of chemical synthesis or analysis. The onium compounds of nitrogen in particular, i.e. the quaternary ammonium compounds, cover a wide spectrum of applications. The quaternary ammonium hydroxides, e.g. tetramethylammonium hydroxide (TMAH) and tetraethylammonium hydroxide (TEAH) are strong organic bases which have been known for many years. Such quaternary ammonium hydroxides have found numerous applications, for example for the titration of acids in organic solvents or as electrolytes in polarography. Aqueous solutions of quaternary ammonium hydroxides, especially of TMAH, are often used as developers for photoresists in printed circuits and in chip manufacture. Often, however, the particular application demands that in addition to the abovementioned ammonium hydroxides, industrially available on a large scale, those carrying larger organic substituents be used, for example when employed as phase transfer catalysts or in the production of zeolites.

Many applications moreover require the ammonium hydroxides to be of high purity, for example to prevent the formation of by-products or any contamination of semiconductor elements. The high purity demanded relates to residual levels of halides, sulfates, carbonates and the like, for example in the manufacture of semiconductor elements. If ammonium hydroxides are used in the preparation of zeolites, the high purity relates particularly to as low an alkali metal ion level as possible.

Various methods of preparing quaternary ammonium hydroxides such as TMAH, TEAH or TPAH are known already. Generally, the quaternary ammonium hydroxides are prepared by electrolysis of a salt of a quaternary ammonium compound in an electrochemical cell which includes one or more membranes capable of exchanging cations. The quaternary ammonium salts customarily employed in such processes comprise halides, carboxylates, carbonates and sulfates.

WO 98/09002 describes the preparation of onium hydroxides in an electrochemical cell. This publication describes an electrodialysis process employing a cell unit which includes four volumes, the cell unit being defined by an anode-side bipolar membrane, a first membrane dividing the cell and a second membrane dividing the cell. Described in detail are cell structures which include various arrangements of bipolar membranes each comprising one anion-selective and one or more cation-selective membranes as cell dividers.

EP 0 824 346 describes a method of purifying hydroxy compounds in an electrochemical cell, where the cell unit comprises a bipolar membrane and a cationic membrane. Also described are cell arrangements which, in addition to the cell based on two membranes, include yet further membranes, anionic membranes as a rule.

WO 98/44169 relates to a method of preparing onium hydroxides from a suitable onium salt and of purifying such onium hydroxides. Described inter alia is an arrangement of electrochemical cells, making use of at least a first electrochemical cell and a second electrochemical cell. The first type of electrochemical cells includes a bipolar membrane and at least one further cell delimiter, possible examples of the at least one further cell delimiter including a nonionic microporous diffusion barrier such as a screen, filter, diaphragm etc. or an ionic cell delimiter such as a cation-selective membrane. The second electrochemical cell can include one or more bipolar membranes and one or more cell dividers, cation-selective membranes and anion-selective membranes being specified as being also within the scope of the invention. According to the patent description, the second cell arrangement serves the purpose of removing undesirable amounts of acid from the solution which was originally fed into the circuit. The use of an electrodialysis unit in which a unit cell includes a bipolar and an anionic membrane, with a bipolar membrane or a cation-selective membrane being located on the anode side between the last anion-selective membrane and the anode, for the purpose of preparing onium hydroxides, is not disclosed in the publication.

J. R. Ochoa, Gomez and M. Tarancon Estrada, in *Journal of Applied Electrochemistry*, 21, (1991), Short Communication, describe the synthesis of quaternary ammonium hydroxides in an electrolytic cell which includes an anion exchange membrane. Via the procedure described in the publication, quaternary ammonium hydroxides are obtained which still include a high halide content.

U.S. Pat. No. 4,578,161 describes a method of preparing quaternary ammonium hydroxides via electrolysis, which makes use of an electrolytic cell which includes an anion exchange membrane. The solutions of quaternary ammonium hydroxides obtained via the described method are likewise distinguished by a high residual bromide content.

U.S. Pat. No. 5,286,354 likewise relates to a method of preparing inorganic hydroxides and alkoxides by electrolysis. The method described relates to the use of an electrolytic cell in which the volumes which contain the respective electrode are separated by an anion exchange membrane. The solutions of inorganic hydroxides obtained via the method described have very high residual bromide contents.

As electrodialytic processes as a rule are carried out using more than just one cell unit, a complex design of a cell unit, as often described in the prior art, results in an expensive and fault-prone system, depending on the number of cell units employed in the electrodialysis apparatus. It is therefore desirable to keep the complexity of the cell unit as low as possible, to keep the costs of the electrodialysis apparatus low and its stability at the highest possible level. Another drawback of the systems and electrodialysis apparatus known from the prior art is that the bulky onium ions, for example quaternary ammonium ions, have to pass through a cation-selective membrane during the electrodialysis process. Given the limited pore size of such a membrane, it is not possible, using the prior art method, to prepare onium hydroxides whose cations are bulky. Hitherto, the preparation of such onium hydroxides therefore required a complex cell design which has an adverse impact on the reliability of the electrodialysis apparatus and on the economic viability of such a preparative method.

Moreover, the cell structures known from the prior art have a further drawback in that product-containing material streams are in direct contact with the anode or cathode. Said contact can result in the formation of impurities in the material streams and in a reduced service life of the anode or cathode material.

It is therefore an object of the present invention to provide a method of preparing onium hydroxides and a method of purifying these, which ensures a simple design of a cell unit, permits the preparation of onium hydroxides having bulky cations and moreover increases the service life of the anode and cathode material while at the same time affording material streams comprising a low level of impurities.

This object is achieved according to the invention by a method which involves the conversion, by means of an electrodialysis process in an electrodialysis apparatus, of a salt of an onium compound into the onium hydroxide, a cell unit of the electrodialysis apparatus comprising a bipolar membrane and an anion-selective membrane, with a bipolar membrane or a cation-selective membrane being located on the anode side between the last anion-selective membrane and the anode.

The invention therefore relates to a method of preparing onium hydroxides of the elements N, S or P by electrodialysis in an electrodialysis apparatus which includes an anode, a cathode and one or more cell units each comprising one acid circuit and one base circuit, wherein a solution of an onium salt of the formula (I)

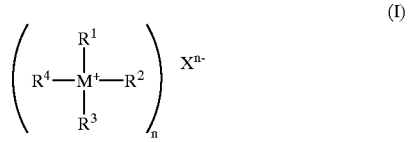

where M is N, S or P; $R^1$, $R^2$, $R^3$ and $R^4$ each, independently of one another, are a linear or branched, saturated or unsaturated aliphatic, cycloaliphatic, araliphatic or aromatic radical having from 1 to 20 C atoms, or two of the radicals $R^1$ to $R^4$ together with M form a heterocyclic ring, $X^{n-}$ is an n-valent anion and n is a number from 1 to 4, is introduced into the base circuit of a cell unit and subjected to an electrodialysis, wherein each cell unit comprises a bipolar membrane and an anion-selective membrane, and a bipolar membrane or a cation-selective membrane is located on the anode side between the last anion-selective membrane and the anode.

In a preferred embodiment of the present invention, M is nitrogen (N).

The radicals $R^1$, $R^2$, $R^3$ and $R^4$ can each, independently of one another, be a linear or branched, saturated or unsaturated aliphatic, cycloaliphatic, araliphatic or aromatic radical having from about 1 to about 20 C atoms. Examples of such radicals are methyl, ethyl, propyl, isopropyl, n-butyl, isobutyl, tert-butyl, pentyl, hexyl, heptyl, octyl, isooctyl, nonyl, decyl, isodecyl, dodecyl, tridecyl, isotridecyl, hexadecyl and octadecyl. $R^1$, $R^2$, $R^3$ and $R^4$ in addition can be substituted by functional groups. Examples of such functional groups are hydroxy or ester groups.

Examples of hydroxy-substituted radicals $R^1$ to $R^4$ are hydroxyethyl, hydroxypropyl, hydroxybutyl, hydroxypentyl and higher homologs thereof and isomers thereof.

In a preferred embodiment of the present invention, $R^1$ to $R^4$ are each, independently of one another, alkyl groups having from 1 to 10 C atoms and especially linear or branched alkyl radicals having from about 2 to about 5 C atoms. In a preferred embodiment of the invention, $R^1$ to $R^4$ are each, independently of one another, propyl, isopropyl or butyl.

The radicals $R^1$ to $R^4$ as defined above can additionally carry alkoxy substituents. Examples of such radicals $R^1$ to $R^4$ are ethoxyethyl, butoxymethyl, butoxybutyl and the like.

X in formula (I) is an n-valent anion, preferably an anion of a Brönsted acid. In a preferred embodiment of the invention, X is F, Cl, Br, I, $SO_4$, $R^5SO_4$, $HSO_4$, $CO_3$, $HCO_3$, $R^5CO_3$ or $R^5CO_2$ or a mixture of two or more of these where $R^5$ is a linear or branched, saturated or unsaturated aliphatic, cycloaliphatic, araliphatic or aromatic radical having from 1 to 20 C atoms.

In a further preferred embodiment, X is an anion from the group consisting of the halogens, especially Cl and Br.

Examples of onium salts of the formula (I) which can be used within the scope of the present invention include tetramethylammonium chloride, tetramethylammonium bromide, tetraethylammonium chloride, tetraethylammonium bromide, tetrapropylammonium chloride, tetrapropylammonium bromide, tetra-n-octylammonium bromide, tetraisopropylammonium chloride, tetraisopropylammonium bromide, trimethylhydroxyethylammonium chloride, trimethylmethoxyethylammonium chloride, tripropylhydroxyethylammonium chloride, tripropylmethoxyethylammonium chloride, triiisopropylhydroxyethylammonium chloride, triisopropylmethoxyethylammonium chloride, dimethyldihydroxyethylammonium chloride, methyltrihydroxyethylammonium chloride, phenyltrimethylammonium chloride, phenyltriethylammonium chloride, benzyltrimethylammonium chloride, benzyltriethylammonium chloride, dimethylpyrrolidonium bromide, dimethylpiperidinium bromide, diisopropyl-imidazolinium bromide, N-alkylpyridinium bromide and the like. The corresponding quaternary ammonium sulfates, carbonates, phosphates and carboxylates can likewise be used.

Examples of quaternary phosphonium halides as described by formula (I) and capable of being used within the scope of the present invention include tetramethylphosphonium bromide, tetraethylphosphonium bromide, tetrapropylphosphonium bromide, tetrabutylphosphonium bromide, trimethylhydroxyethylphosphonium bromide, dimethyldihydroxyethylphosphonium bromide, methyltrihydroxyethylphosphonium bromide, phenyltrimethylphosphonium bromide, phenyltriethylphosphonium bromide or benzyltrimethylphosphonium bromide. Equally capable of being used are the abovementioned compounds in which the anion present is an anion previously mentioned within the context of the description of formula (I).

In a preferred embodiment of the present invention, the onium salt used is tetrapropylammonium bromide.

The method according to the invention is implemented in electrodialysis apparatuses comprising a multiplicity of thin membranes. Electrodialysis apparatuses customarily are of stack-type construction. Such a stack as a rule comprises electrodes (anodes and cathode) at both ends of the stack and a series of membranes and seals which form a multiplicity of separate volumes which are separated from one another by the membranes. Often, the volumes containing the electrodes are filled with electrolyte fluids which are customarily referred to as anolyte and catholyte.

The stack between the electrodes often includes a multiplicity of repeating membrane arrangements. A single membrane sequence repeating a number of times for each stack is customarily referred to, especially within the context of the present text, as a cell unit. Such a cell unit as a rule has a plurality of parallel volumes between the individual membranes forming the cell unit. A solution to be subjected to electrodialysis is fed in, as a rule, through a number of feeders, said number being defined by the number of the volumes of the cell units of the entire stack. Stacks forming the totality of the electrodialysis apparatus can, for example, include just one type of cell unit, but alternatively a number of different types of cell units can be present in each stack.

An electrodialysis apparatus as used within the scope of the present invention includes one or more cell units of particularly simple design. The number m of the cell units employed per electrodialysis apparatus can be up to about 1000, being between about 50 and about 150 in a preferred embodiment of the present invention, for example being about 100.

A cell unit employed within the scope of the inventive method comprises a bipolar membrane and an anion-selective membrane.

Bipolar membranes include an anion-selective and a cation-selective layer of an ion exchange material. So as to be able to dissociate water, the layers of the bipolar membrane must be oriented in such a way that the anion-selective membrane layer is situated toward the anode and the cation-selective membrane layer is situated toward the cathode. If a current flows through such an arrangement, a water layer situated between the two membranes of the bipolar membrane is dissociated into hydroxyl ions on the anode side and protons on the cathode side.

A further component of the cell unit is in the form of an anion-selective membrane. The anion-selective membrane is disposed between the bipolar membrane and the anode, i.e. on the anode side relative to the bipolar membrane.

BRIEF DESCRIPTION OF THE DRAWINGS

FIG. 1 illustrates the design of a cell unit employed in the method according to the invention. Generated via the dissociation of water by a bipolar membrane (1) in the electric field situated between cathode (2) and anode (3)a are $H^+$ and $OH^-$ ions. Disposed on the anode side relative to the bipolar membrane is an anion exchange membrane (4) which is permeable to anions $X^-$. The volume located between bipolar membrane and anion exchange membrane is now charged with the onium salt MX (5). During the electrodialysis process, the anion $X^-$ migrates in the electric field between cathode (2) and anode (3) through the anion exchange membrane toward the anode. The cation $M^+$ is held back by the anion exchange membrane. As the electrodialysis progresses, the only remaining counter ions for $M^+$ found in the volume between bipolar membrane (1) and anion exchange membrane (4) are $OH^-$ ions. The volume enclosed by the bipolar membrane (1) and the anion exchange membrane (4) is also referred to as "base circuit" within the context of the present text.

On the anode side relative to the anion exchange membrane, the anion $X^-$ is able to coordinate with a proton generated in the bipolar membrane (1) of the next cell unit.

Figure 1:
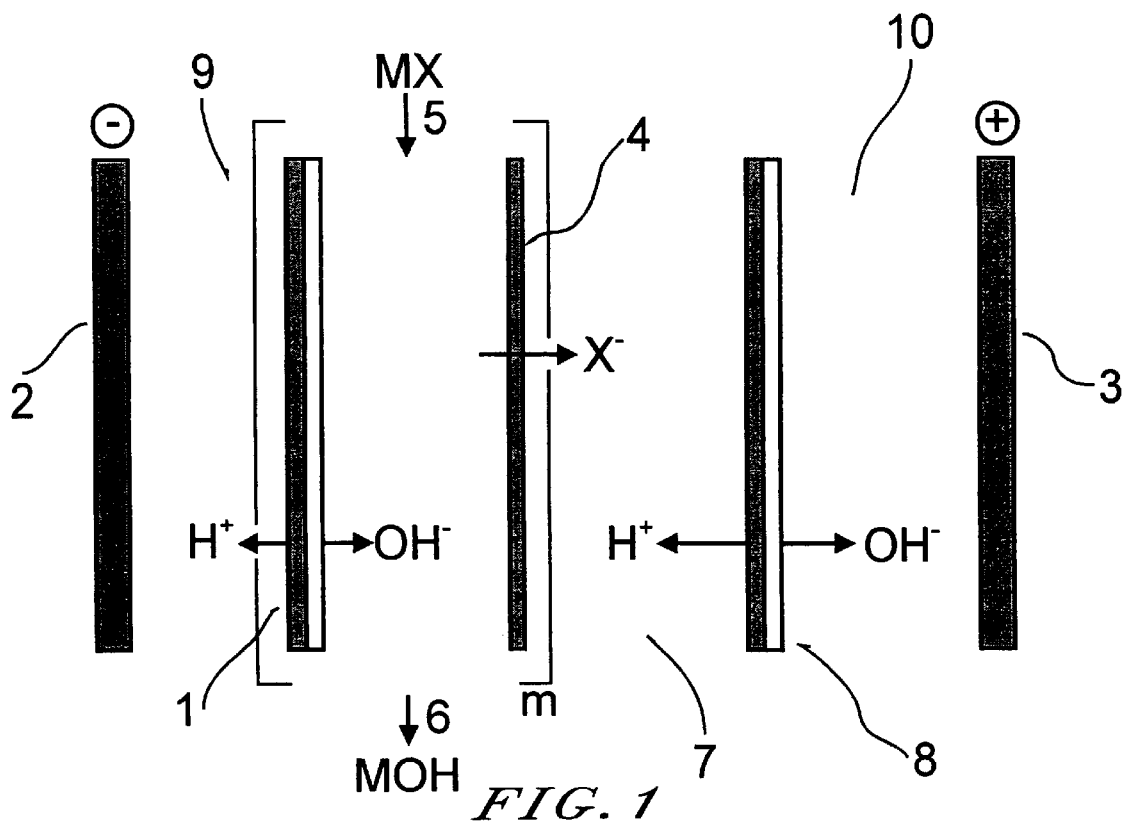
FIG. 1 illustrates the design of a cell unit employed in the method according to the invention.

According to the invention, as shown in FIG. 1, a further bipolar membrane (8) is inserted between the last anode-side anion exchange membrane (4) and the anode (3). This serves to protect the anode against corrosion and to prevent chemical contamination. The volume (7) formed by the anion exchange membrane (4) and a subsequent bipolar membrane (1 or 8) is referred to as "acid circuit" within the context of the present text. The volumes situated between cathode (2) and anode (3) and the respective next bipolar membrane (1 or 8) are referred to as catholyte (9) and anolyte (10). The number m is the number of cell units enclosed in square brackets in FIG. 1.

Figure 2:
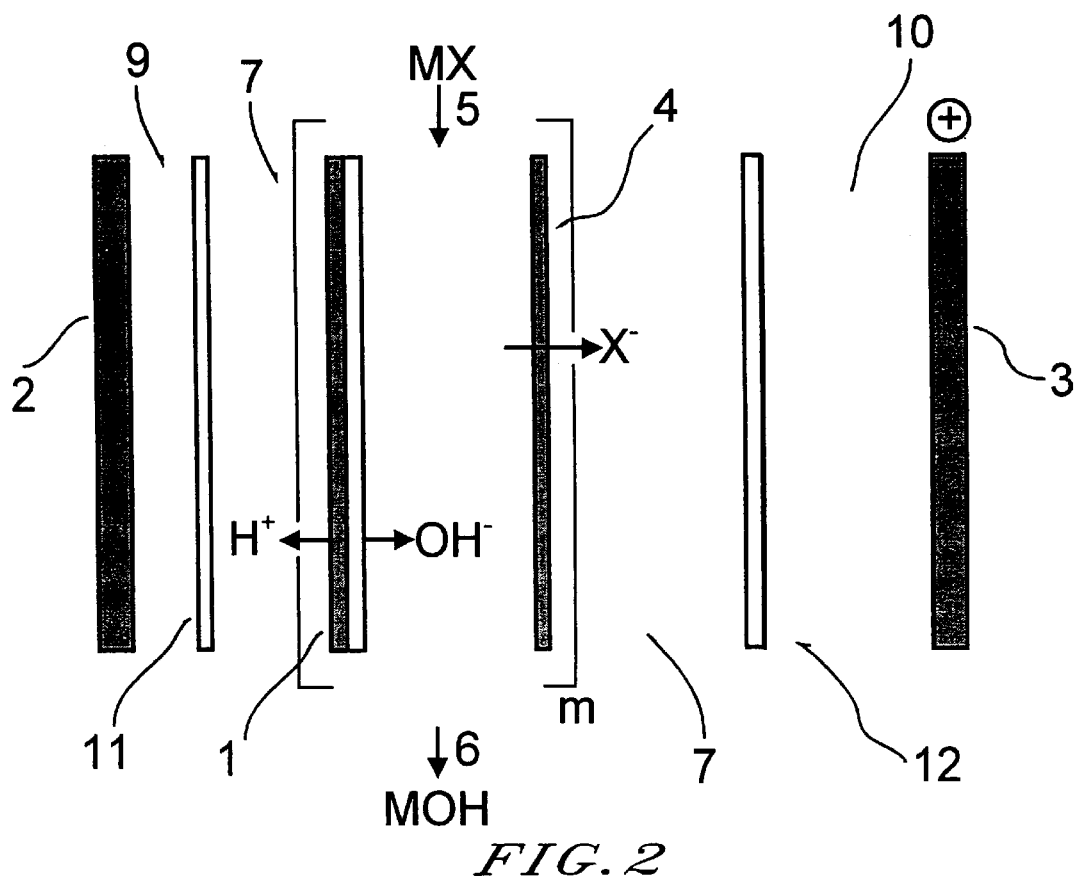
FIG. 2 shows a further cell unit employed within the context of a preferred embodiment in the method according to the invention.

FIG. 2 shows a further cell unit employed within the context of a preferred embodiment in the method according to the invention. In contrast to the cell structure described in FIG. 1, the bipolar membrane (8) is absent, and limiting membranes are present on the cathode side and the anode side in the form of a cation exchange membrane (11) and (12), respectively. The membrane arrangement described in FIG. 2 prevents direct contact of the compounds in the circuits denoted by (7) with the anode and the cathode, respectively, thereby allowing undesirable side reactions or contamination of the electrodes to be prevented.

In a preferred embodiment of the invention, the cathode of the electrodialysis apparatus is separated therefore from the first cell unit on the cathode side by a cation-selective membrane.

In a further preferred embodiment of the invention, the anode of the electrodialysis apparatus is separated from the first cell unit on the anode side by a cation-selective membrane, and likewise the cathode of the electrodialysis apparatus is separated from the first cell unit on the cathode side by a cation-selective membrane.

Within the scope of the method according to the invention, a solution of an onium salt MX (5) is then introduced into the base circuit of the cell units present in the electrodialysis apparatus. The electrodialysis is carried out at a current density of from about 1 to about 20 $A/dm^2$, particularly at from about 5 to about 10 $A/dm^2$.

The temperature during the electrodialysis is from about 20 to about 60° C., in particular from about 30 to about 50° C., for example about 40° C.

The method according to the invention is usually employed as a batch method.

This involves carrying out the electrodialysis over a period of from about 12 to 100 hours, in particular from about 20 to about 60 hours. In so doing, the conductivity and current intensity can remain constant over the entire run time, although it is equally possible for the method according to the invention to be implemented using parameters that can vary during the run time.

The onium salt MX is, as a rule, fed in from the base circuit onward in the form of a solution in a protic solvent or a mixture of two or more protic solvents. Examples of suitable protic solvents include water or alcohols such as methanol, ethanol, propanol, butanol and the like. Where appropriate, the solvent used can be a mixture of water and a water-soluble OH-carrying compound or of a mixture of two or more such compounds.

The concentration of the onium salt fed in in the protic solvent of the mixture of two or more protic solvents is from about 0.1 to about 70 wt %, preferably from about 1 to about 60 wt %. In a preferred embodiment of the present invention, the concentration is from about 5 to 40 wt %, for example about 10, 15 or 20 wt %.

The anolyte circuit and catholyte circuit can, for example, be filled with water or the solvent used for the onium salt, although it has proved advantageous for both circuits to be charged with a Brönsted acid, for example a sulfuric acid solution having a concentration from about 1 to 10 wt %.

To adjust the conductivity in a preferred embodiment of the invention, the acid circuit is charged with a solution having a strength of from about 0.1 to 1 wt % of an acid HY, where Y can be any anion of a Brönsted acid, but in a preferred embodiment of the present invention is the anion X of the onium salt of MX.

Suitable as bipolar membranes are all commercially available membranes such as BP-1 (manufactured by Tokuyama Corp.) or the types prepared on a polysulfone basis by Aqualytics.

The anion exchange membranes used can likewise be of any known type. In a preferred embodiment of the present invention, the types Necsepta AM3, ACLE-SP, AMH or AHA-2 (manufactured by Tokuyama Corp.) or Selemion AMH or AMP (manufactured by Asahi Glass) or Ionac membranes of the MA series, e.g. MA 3148, 3236 or 3475 (manufactured by SYBRON).

The cation exchange membranes used can be of any customary type. Within the scope of a preferred embodiment, the membranes CMH, CMX, C66-10F (manufactured by Tokuyama Corp.) or membranes of the NAFION series, e.g. 117, 350 or 450, (manufactured by DuPont) are used.

A large number of materials can be used as anode materials. For example, metal anodes such as titanium-coated electrodes, tantalum, zirconium, hafnium or alloys thereof can be employed. In general, the anodes carry a nonpassivable catalytic film which contains noble metals such as platinum, iridium, rhodium or alloys thereof, or a mixture of electrically conductive oxides, at least one of the oxides comprising a noble metal such as platinum, iridium, ruthenium, palladium or rhodium.

The cathodes can likewise include any conductive material. Preferably, the conductive material is stable under the prevailing conditions, and the cathode includes a material which has a small overpotential with respect to hydrogen generation. Examples of materials which can be used as cathodes comprise stainless steel, nickel, titanium, graphite or iron.

The inventive method described within the context of the present text can be used for the preparation of onium salts of the elements N, S and P. A further possible application, however, is to subject onium hydroxides of these elements to purification. To this end, the base circuit of the cell unit is charged with an appropriate solution of an onium hydroxide which contains impurities that can dissociate in water, and is subjected to electrodialysis.

The invention therefore also relates to a method of purifying onium hydroxides of the elements N, S or P by electrodialysis in an electrodialysis apparatus comprising an anode, a cathode and one or more cell units which each include an acid circuit and a base circuit wherein a solution of an onium hydroxide of the formula I containing impurities that can dissociate in water, in which formula I M is N, S or P; $R^1$, $R^2$, $R^3$ and $R^4$ each, independently of one another, are a linear or branched, saturated or unsaturated aliphatic, cycloaliphatic, araliphatic or aromatic radical having from 1 to 20 C atoms, X is OH and n is the number 1, is introduced into the base circuit of the cell unit and subjected to an electrodialysis, wherein each cell unit comprises a bipolar membrane and an anion-selective membrane, a bipolar membrane or a cation-selective membrane being located on the anode side between the last anion-selective membrane and the anode.

The invention is explained below by means of further examples:

EXAMPLES

Example 1

In a three-circuit electrodialysis cell corresponding to FIG. 2, consisting of a ruthenium mixed oxide anode, a steel cathode and five cell units, bipolar membranes (type polysulfone, Aqualytics), anion exchange membranes (ACLE-SP Tokuyama Corp.) and cation exchange membranes (C66-10F, Tokuyama Corp.), the base circuit was charged with a 10 wt % tetrapropylammonium bromide solution. The acid circuit was charged with a 0.6% strength HBr solution, while a 5% strength sulfuric acid solution was circulating in the anolyte and catholyte circuit. The temperature in all these circuits was 40° C. At a current intensity of 8 A/dm$^2$ and a conductivity of 100 mS in the acid circuit, an 8.74% strength tetrapropylammoniumhydroxide solution with a residual bromide content of 27 ppm was obtained. The residual Na and K ion content was $\leq 1$ ppm.

Example 2

Under conditions identical to those in Example 1, but at 5.7 A/dm$^2$, an 8.50% strength tetrapropylammoniumhydroxide solution with a residual bromide content of 20 ppm is obtained. The residual Na and K ion content is $\leq 1$ ppm.

Example 3

Under conditions identical to those in Example 1, a 10 wt % strength tetrabutylammonium bromide solution was electrodialyzed. At a current intensity of 8 A/dm$^2$, 8.50% strength tetrabutylammonium hydroxide solution with a residual bromide content of 20 ppm was obtained.

We claim:

1. A method of preparing onium hydroxides of the elements N, S or P by electrodialysis in an electrodialysis apparatus which includes anode (3), a cathode (2) and one or more cell units each comprising one acid circuit (7) and one base circuit, wherein a solution (5) of an onium salt of the formula I

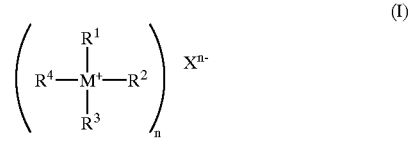

wherein M is N, S or P; $R^1$, $R^2$, $R^3$ and $R^4$ each, independently of one another, are a linear or branched, saturated or unsaturated aliphatic, cycloaliphatic, araliphatic or aromatic radical which is unsubstituted or which may be substituted by functional groups and has from 1 to 30 C atoms, or two of the radicals $R^1$ to $R^4$ together with M form a heterocyclic ring, $X^{n-}$ is an n-valent anion and n is a number from 1 to 4, is introduced into the base circuit of the cell unit and subjected to an electrodialysis, wherein each cell unit comprises a bipolar membrane (1) and an anion-selective membrane (4), and a bipolar membrane (8) or a cation-selective membrane (12) is located on the anode side between the last ion-selective membrane and the anode (3), and the cathode (2) of the electrodialysis apparatus is separated from the first cell unit on the cathode side by a cation selective membrane (11).

2. A method as claimed in claim 1, wherein $R^1$, $R^2$, $R^3$ and $R^4$ each, independently of one another, are a linear or branched aliphatic radical having from 1 to 4 C atoms.

3. A method as claimed in claim 1, wherein X is the anion of a Brönsted acid.

4. A method as claimed in claim 1, wherein X is F, Cl, Br, I, SO$_4$, R$^5$SO$_4$, HSO$_4$, CO$_3$, HCO$_3$, R$^5$CO$_3$ or R$^5$CO$_2$ or a mixture of two or more of these and R$^5$ is a linear or branched, saturated or unsaturated aliphatic, cycloaliphatic, araliphatic or aromatic radical having from 1 to 30 C atoms.

5. A method as claimed in claim 1, wherein M is N.

6. A method as claimed in claim 1, wherein the onium salt is dissolved in a protic solvent or a mixture of two or more protic solvents.

7. A method as claimed in claim 1, wherein the onium salt is dissolved in a mixture of water and a water-soluble OH-carrying compound or a mixture of two or more such compounds.

8. A method of preparing onium hydroxides of the elements N, S or P by electrodialysis in an electrodialysis apparatus which includes an anode (3), a cathode (2) and one or more cell units each comprising one acid circuit (7) and one base circuit, wherein a solution (5) of an onium salt of the formula I

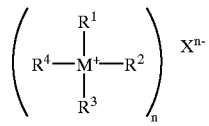
(I)

wherein M is N, S or P; $R^1$, $R^2$, $R^3$ and $R^4$ each, independently of one another, are a linear or branched, saturated or unsaturated aliphatic, cycloaliphatic, araliphatic or aromatic radical which is unsubstituted or which may be substituted by functional groups and has from 1 to 30 C atoms, or two of the radicals $R^1$ to $R^4$ together with M form a heterocyclic ring, $X^{n-}$ is an n-valent anion and n is a number from 1 to 4, is introduced into the base circuit of the cell unit and subjected to an electrodialysis, wherein each cell unit comprises a bipolar membrane (1) and an anion-selective membrane (4), and a bipolar membrane (8) or a cation-selective membrane (12) is located on the anode side between the last ion-selective membrane and the anode (3), and the cathode (2) of the electrodialysis apparatus is separated from the first cell unit on the cathode side by a cation selective membrane (11), and wherein the anode (3) of the electrodialysis apparatus is separated from the first cell unit on the anode side by a cation-selective membrane (12).

9. A method as claimed in claim 8, wherein $R^1$, $R^2$, $R^3$ and $R^4$ each, independently of one another, are a linear or branched aliphatic radical having from 1 to 4 C atoms.

10. A method as claimed in claim 8, wherein X is the anion of a Brönsted acid.

11. A method as claimed in claim 8, wherein X is F, Cl, Br, I, $SO_4$, $R^5SO_4$, $HSO_4$, $CO_3$, $HCO_3$, $R^5CO_3$ or $R^5CO_2$ or a mixture of two or more of these and $R^5$ is a linear or branched, saturated or unsaturated aliphatic, cycloaliphatic, araliphatic or aromatic radical having from 1 to 30 C atoms.

12. A method as claimed in claim 8, wherein M is N.

13. A method as claimed in claim 8, wherein the onium salt is dissolved in a protic solvent or a mixture of two or more protic solvents.

14. A method as claimed in claim 8, wherein the onium salt is dissolved in a mixture of water and water-soluble OH-carrying compound or a mixture of two or more such compounds.

15. A method of purifying onium hydroxides of the elements N, S or P by electrodialysis in an electrodialysis apparatus comprising an anode (3), a cathode (2) and one or more cell units which each include an acid circuit (7) and a base circuit wherein a solution of an onium hydroxide of the formula I containing impurities that can dissociate in water,

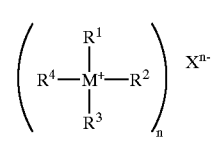
(I)

wherein M is N, S or P; $R^1$, $R^2$, $R^3$ and $R^4$ each, independently of one another, are a linear or branched, saturated or unsaturated aliphatic, cycloaliphatic, araliphatic or aromatic radical having from 1 to 20 C atoms, X is OH and n is the number 1, is introduced into the base circuit of the cell unit and subjected to an electrodialysis, wherein each cell unit comprises a bipolar membrane (1) and an anion-selective membrane (4), and a bipolar membrane (8) or a cation-selective membrane (12) is located on the anode side between the last anion-selective membrane and the anode (3), and the cathode (2) of the electrodialysis apparatus is separated from the first cell unit on the cathode side by a cation-selective membrane (11).

16. A method as claimed in claim 15, wherein $R^1$, $R^2$, $R^3$ and $R^4$ each, independently of one another, are a linear or branched radical having from 1 to 4 C atoms.

17. A method as claimed in claim 15, wherein X is the anion of a Brönsted acid.

18. A method as claimed in claim 15, wherein M is N.

19. A method as claimed in claim 15, wherein the onium salt is dissolved in a protic solvent or a mixture of two or more protic solvents.

20. A method as claimed in claim 15, wherein the onium salt is dissolved in a mixture of water and a water-soluble OH-carrying compound or a mixture of two or more such compounds.

21. A method of purifying onium hydroxides of the elements N, S or P by electrodialysis in an electrodialysis apparatus comprising an anode (3), a cathode (2) and one or more cell units which each include an acid circuit (7) and a base circuit wherein a solution of an onium hydroxide of the formula I containing impurities that can dissociate in water,

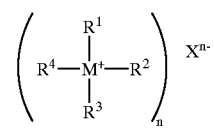
(I)

wherein M is N, S or P; $R^1$, $R^2$, $R^3$ and $R^4$ each, independently of one another, are a linear or branched, saturated or unsaturated aliphatic, cycloaliphatic, araliphatic or aromatic radical having from 1 to 20 C atoms, X is OH and n is the number 1, is introduced into the base circuit of the cell unit and subjected to an electrodialysis, wherein each cell unit comprises a bipolar membrane (1) and an anion-selective membrane (4), and a bipolar membrane (8) or a cation-selective membrane (12) is located on the anode side between the last anion-selective membrane and the anode (3), and the cathode (2) of the electrodialysis apparatus is separated from the first cell unit on the cathode side by a cation-selective membrane (11), and wherein the anode (3) of the electrodialysis apparatus is separated from the first cell unit on the anode side by a cation-selective membrane (12).

22. A method as claimed in claim 21, wherein X is the anion of a Brönsted acid.

23. A method as claimed in claim 21, wherein M is N.

24. A method as claimed in claim 21, wherein the onium salt is dissolved in a protic solvent or a mixture of two or more protic solvents.

25. A method as claimed in claim 21, wherein the onium salt is dissolved in a mixture of water and a water-soluble OH-carrying compound or a mixture of two or more such compounds.

* * * * *